(12) United States Patent
Porter et al.

(10) Patent No.: US 6,558,162 B1
(45) Date of Patent: May 6, 2003

(54) HEALING COMPONENTS FOR USE IN TAKING IMPRESSIONS AND METHODS FOR MAKING THE SAME

(75) Inventors: Stephan S. Porter, Palm Beach Gardens, FL (US); Theodore M. Powell, Jupiter, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

(21) Appl. No.: 09/710,208

(22) Filed: Nov. 10, 2000

Related U.S. Application Data
(60) Provisional application No. 60/164,521, filed on Nov. 10, 1999.

(51) Int. Cl.[7] ............................................. A61C 8/00
(52) U.S. Cl. ...................................... 433/173; 433/213
(58) Field of Search ............................... 433/172, 173, 433/174, 213, 214

(56) References Cited

U.S. PATENT DOCUMENTS

| | | | |
|---|---|---|---|
| 3,958,471 A | 5/1976 | Muller | |
| 4,011,602 A | 3/1977 | Rybicki et al. | |
| 4,086,701 A | 5/1978 | Kawahara et al. | |
| 4,177,562 A | 12/1979 | Miller et al. | |
| 4,306,862 A | 12/1981 | Knox | |
| 4,341,312 A | 7/1982 | Scholer | |
| 4,547,157 A | 10/1985 | Driskell | |
| 4,624,673 A | 11/1986 | Meyer | |
| 4,713,004 A | 12/1987 | Linkow et al. | |
| 4,758,161 A | 7/1988 | Niznick | |
| 4,767,331 A | 8/1988 | Hoe | |
| 4,772,204 A | 9/1988 | Soderberg | |
| 4,842,518 A | 6/1989 | Linkow et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | * 8/1989 | Lazzara et al. | ............... 433/173 |
| 4,872,839 A | 10/1989 | Brajnovic | |
| 4,906,191 A | 3/1990 | Soderberg | |
| 4,955,811 A | 9/1990 | Lazzara et al. | |
| 4,988,297 A | 1/1991 | Lazzara et al. | |
| 4,988,298 A | 1/1991 | Lazzara et al. | |
| 5,000,685 A | 3/1991 | Brajnovic | |
| 5,006,069 A | 4/1991 | Lazzara et al. | |
| 5,015,186 A | 5/1991 | Detsch | |
| 5,030,096 A | 7/1991 | Hurson et al. | |
| 5,035,619 A | 7/1991 | Daftary | |
| 5,040,983 A | 8/1991 | Binon | |
| 5,064,375 A | 11/1991 | Jörnéus | |
| 5,071,351 A | 12/1991 | Green, Jr. et al. | |
| 5,073,111 A | 12/1991 | Daftary | |

(List continued on next page.)

FOREIGN PATENT DOCUMENTS

| | | |
|---|---|---|
| DE | 2 114 323 | 3/1971 |
| DE | 3 531 389 A1 | 3/1987 |
| DE | 4 028 855 A1 | 3/1992 |

(List continued on next page.)

OTHER PUBLICATIONS

Price List; *Stryker Dental Implants*, Jun. 1, 1993, 4 sheets.
Catalog; *Impla–Med*, Mar. 1991, 16 pp.

(List continued on next page.)

*Primary Examiner*—Ralph A. Lewis
(74) *Attorney, Agent, or Firm*—Jenkens & Gilchrist

(57) ABSTRACT

The present invention provides a healing abutment for attachment to a dental implant with information markers provided thereon and a method for making the same. The implant has an apical end installed into a jawbone having overlying gingiva and a gingival end near an interface of the gingiva and the jawbone with a hexagonal boss thereon. The healing element comprises information markers for determining the orientation of said hexagonal boss, the diameter of said healing element, the height of said healing element, and the size of said implant.

42 Claims, 9 Drawing Sheets

U.S. PATENT DOCUMENTS

| | | |
|---|---|---|
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,135,395 A | 8/1992 | Marlin |
| 5,145,371 A | 9/1992 | Jörnéus |
| 5,145,372 A | 9/1992 | Daftary et al. |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,246,370 A | 9/1993 | Coatoam |
| 5,281,140 A | 1/1994 | Niznick |
| 5,286,195 A | 2/1994 | Clostermann |
| 5,292,252 A | 3/1994 | Nickerson et al. |
| 5,297,963 A | 3/1994 | Dafatry |
| 5,312,254 A | 5/1994 | Rosenlicht |
| 5,316,476 A | 5/1994 | Krauser |
| 5,322,436 A * | 6/1994 | Horng et al. ................. 433/23 |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A * | 8/1994 | Wu et al. ................... 433/213 |
| 5,344,457 A | 9/1994 | Pilliar et al. |
| 5,362,234 A | 11/1994 | Salazar et al. |
| 5,362,235 A | 11/1994 | Daftary |
| 5,368,483 A | 11/1994 | Sutter et al. |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,452,219 A * | 9/1995 | Dehoff et al. .......... 364/474.05 |
| 5,458,488 A | 10/1995 | Chalifoux |
| 5,476,382 A | 12/1995 | Daftary |
| 5,476,383 A | 12/1995 | Beaty et al. |
| 5,492,471 A * | 2/1996 | Singer ........................ 433/172 |
| 5,527,182 A | 6/1996 | Willoughby |
| 5,533,898 A | 7/1996 | Mena |
| 5,538,426 A | 7/1996 | Harding et al. |
| 5,547,377 A * | 8/1996 | Daftary ...................... 433/172 |
| 5,564,921 A | 10/1996 | Marlin |
| 5,564,924 A | 10/1996 | Kwan |
| 5,651,675 A | 7/1997 | Singer |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,733,123 A * | 3/1998 | Blacklock et al. .......... 433/173 |
| 5,759,036 A | 6/1998 | Hinds |
| 5,810,592 A * | 9/1998 | Daftary ...................... 433/173 |
| 5,813,858 A | 9/1998 | Singer |
| 5,846,079 A | 12/1998 | Knode |
| 5,851,115 A | 12/1998 | Carlsson et al. |
| 5,857,853 A * | 1/1999 | van Nifterick et al. ...... 433/213 |
| 5,871,358 A * | 2/1999 | Ingber et al. ............... 433/213 |
| 5,873,722 A | 2/1999 | Lazzara et al. |
| 5,938,443 A | 8/1999 | Lazzara et al. |
| 5,964,591 A | 10/1999 | Beaty et al. |
| 6,120,293 A | 9/2000 | Lazzara et al. |
| 6,129,548 A | 10/2000 | Lazzara et al. |
| 6,135,773 A | 10/2000 | Lazzara |
| 6,257,890 B1 * | 7/2001 | Khoury et al. .............. 433/173 |
| 6,273,720 B1 * | 8/2001 | Spalten ....................... 433/173 |
| 6,312,260 B1 * | 11/2001 | Kumar et al. ............... 433/174 |

FOREIGN PATENT DOCUMENTS

| | | |
|---|---|---|
| EP | 0 442 855 A1 | 8/1991 |
| EP | 0 657 146 A1 | 6/1995 |
| EP | 0 727 193 A1 | 8/1996 |
| EP | 0 747 017 A2 | 12/1996 |
| FR | 2 759 896 | 8/1998 |
| GB | 1 291 470 | 10/1972 |
| WO | 85/02337 | 6/1985 |

OTHER PUBLICATIONS

Catalog Data Sheet; *Stryker Dental Implants*, "Surgical Flexibility Prosthetic Simplicity, Stryker Universal Hextop Component™," "Stryker Precision Cylinder Implant," 8 sheets; date unknown.

Catalog; *Oratronics, Inc.*, "Options for Oral Implantology . . . Endosseous Tri–Dimensional T–3D Oral Implant Healing System (OIHS)," 1978, 8 pp.

Perri DDS et al; "Single Tooth Implants," *CDA Journal*, vol. 17(3), Mar. 1989, 4 pp.

Lewis, S.G. et al; "The 'UCLA' Abutment," *The International Journal of Oral & Maxillofacial Implants*, vol. 3(3), 1988, 7 pp.

Lewis, S.G. et al; "Single Tooth Implant Supported Restorations," *The International Journal of Oral & Maxillofacial Implants*, vol. 3(1), 1988, 6 pp.

Lazzara, Richard J., DMD, MScD; "Managing the Soft Tissue Margin: The Key to Implant Aesthetics," *Practical Periodontics and Aesthetic Dentistry*, vol. 5(5), Jun./Jul. 1993, 8 pp.

Product Catalog; "EsthetiCone™ SysteM Components," *Prosthetics*, 1991, 1 pg.

Manual; "New Bio–Esthetic™ Technique Manual," *Steri-Oss Dental Implants*, 1195, 6 pp.

Adell et al; "A 15–year study of osseointegrated implants in the treatment of the edentulous jaw," *International Journal Oral Surgery*, vol. 10, 1981, pp. 387–416.

Catalog; "The DIA Anatomic Abutment System™," *Dental Imaging Associates, Inc.*, Oct. 9, 1991, 12 pp.

Exhibit A; Drawing of a Healing Abutment, 1 pg.

Exhibit B; Drawing of Implant Impression Coping Assembly, 3 pp.

Exhibit C; Drawing of One–Piece Healing Abutment (made of DELRIN.TM).

Brochure; "1989 Core–Vent Implant Symposium," *Core-Vent Corporation*, Mar. 1988, 1 pg.

Publication; "Osstium," *Steri–Oss Dental Implants*, Fall 1995, 8 pp.

Catalog; "Hexed–Head™ Implant System," *IMTEC Corporation*, Spring 1993, 11 pp.

* cited by examiner

HEALING COMPONENTS FOR USE IN TAKING IMPRESSIONS AND METHODS FOR MAKING THE SAME

CROSS-REFERENCE TO RELATED APPLICATIONS

This application claims the benefit of priority of United States provisional patent application Ser. No. 60/164,521, filed Nov. 10, 1999 and entitled "Healing Components For Use In Taking Impressions And Methods For Making The Same."

TECHNICAL FIELD OF INVENTION

The present invention relates generally to a healing component in a dental implant system and a method for making the same. More particularly, the present invention relates to the use of information markers on the exterior of a healing abutment to eliminate the need for an impression coping in the dental implant system and quicken the time required to construct permanent dental components.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced. During the typical second stage of dental restoration, the healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is taken. The impression coping may be a "pick-up" type impression coping or a "transfer" type impression coping, both known in the art. After these second stage processes, a dental laboratory creates a prosthesis to be permanently secured to the dental implant from the impression that was made.

In addition to the method that uses the impression material and mold to manually develop a prosthesis, systems exist that utilize scanning technology to assist in generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and surrounding area is scanned to produce the permanent components. Third, a dentist can scan the stone model of the dental region that was formed from the impression material and mold.

Three basic scanning techniques exist, laser scanning, photographic imaging and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer aided design ("CAD") package.

The utilization of a CAD program, as disclosed in U.S. Pat. No. 5,338,198, (Wu), whose disclosure is incorporated by reference herein, is one method of scanning a dental region to create a three dimensional model. Preferably, after the impression is taken of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known location in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known means.

Photographic imaging can also used to scan impression material, a stone model or to scan directly in the mouth. For example, one system takes photographs at multiple angles in one exposure to scan a dental region, create a model and manufacture a prosthetic tooth. As disclosed in U.S. Pat. No. 5,851,115, (Carlsson), whose disclosure is incorporated by reference herein, this process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position and other details of the model, the ultimate step is the transmission of the data to a computer for manufacturing.

A third scanning measure uses mechanical sensing. A mechanical contour sensing device, as disclosed in U.S. Pat. No. 5,652,709 (Andersson), whose disclosure is incorporated by reference herein, is another method used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer then compresses the data for storage and/or transmission to the milling equipment.

SUMMARY OF THE INVENTION

The present invention provides healing abutments comprising information markers and methods of forming the same. During the second stage of dental restoration, a healing abutment is non-rotationally fastened to the implant with an abutment-attaching bolt. According to the invention, the information markers eliminate the need for an impression coping within the implant system. Further, such a system eliminates the need to remove the healing abutment until the permanent components are ready to be installed in the patient's mouth.

Information markers located on at least one surface of the healing abutments of the present invention allow the dentist to determine the size of the healing abutment and the size and orientation of the implant seated below the healing abutment. Specifically, the information markers, when used in combination, permit identification of the healing abutment height, healing abutment diameter, dimensions of the attached implant seating surface, and implant hex orientation. A common type of dental implant has a hexagonal post or boss (commonly called a "hex") on its gingival end that is adapted to mate with a cooperating socket on a restoration component.

It is contemplated in accordance with one embodiment of the present invention that these information markers may be disposed on the top and/or the sides of the healing abutment. It is also contemplated in accordance with one embodiment of the present invention that the information markers may extend outward (positive) from or inward (negative) towards the healing abutment. It is also contemplated that a healing abutment of one embodiment of the present invention may comprise a combination of positive and negative information markers. It is further contemplated that the top or side surface of the healing abutment can be etched or defined with a polygonal, numerical, or line marking to indicate height, location and orientation of the underlying hex, abutment and/or implant.

In one embodiment of the present invention, the positive or negative information markers correspond to the height of the abutment to be captured in an impression or subsequent scan. For example, a 6-mm tall healing abutment could possess 6 information markers on the top or side surface of the healing abutment. A 4-mm tall healing abutment could possess 4 information markers and a 2-mm tall healing abutment may possess 2 information markers. This marking system could be altered to decrease the quantity of information markers required on the top or side surface of the healing abutment. For example, it is contemplated in accordance with the present invention that the use of 3 information markers on the top or side surface could represent a 6-mm tall healing abutment, 2 information markers to indicate a 4 mm tall abutment, and 1 marker to indicate a 2-mm tall abutment.

It is also contemplated that the healing abutments of the present invention can be manufactured in sets of healing abutments, each set having healing abutments of the same diameter but different healing abutment heights. Different sets of healing abutments would have healing abutments with different diameters. For example, a first set of healing abutments may contain 3 healing abutments, one abutment of 2 mm, 4 mm, and 6 mm height, respectively, and each with a diameter of 4 mm. A second set of healing abutments would also have abutments with heights of 2 mm, 4 mm, and 6 mm, but these abutments would have a diameter of 5 mm. Information markers would distinguish not only between the first and second set of healing abutments, but also between the three healing abutments within each set.

Several different types of information markers are used on the healing abutments of the present invention to indicate and correspond to various characteristics of the implant and/or the healing abutment. The information markers are placed on the healing abutment in order to identify characteristics such as the diameter of the healing abutment, the diameter of the implant's seating surface (and, consequently, the size of the hex), the height of the healing abutment, and the orientation of the hex (and, thus, the angle of the underlying implant).

Machined notches are one example of information markers. The quantity of notches and the location on the top and/or side surface of the healing implant can identify, for example, the height and diameter of the healing abutment. A numeral may also appear on the top or side surface of the healing implant as an information marker. For example, a "4" might indicate a 4 mm tall healing abutment or a 4 mm diameter healing abutment. A barcode can also be disposed on the top or side surface of the healing abutment of the present invention. This barcode is pre-coded with most of the dimensional variables of a particular healing abutment. The laboratory or dentist would only then have to use a barcode reader and display to obtain all of the required information about the healing abutment. If a dentist utilizes a barcode reader to obtain this information, it would only be necessary to identify the angular orientation of the implant hex by information markers on the top or side surface of the healing abutment.

The top and/or side surface of the healing abutment could also contain recessed dimples or raised pimples. These types of information markers are used to identify, for example, the height of the healing abutment and/or the orientation of the hex. An etched or machined polygon (e.g., triangle, pentagon, hexagon, quadrilateral, etc.) is used to signify the location or existence of several of the healing abutment and/or implant variables. For example, the location of an etched hexagon on the surface of a healing abutment of the present invention can indicate, for example, the exact orientation of the underlying hex. Another type of information marker to allow indication of healing abutment or implant variables is an etched or raised line on the top and/or side surfaces of the healing implant. The number and location of these lines can indicate, for example, the height of the healing implant or the diameter of the implant or healing abutment. It is contemplated in accordance with the present invention that the different types of information markers can be used, either alone or in combination, to help the dentist and the laboratory determine the different variables of the healing abutment and the implant.

An impression of the mouth is taken with the healing abutment mounted on the implant. The impression process creates a "negative" image of the information markers in the impression material that change the physical shape of the top or side surface. Of course, the etched markers would not create a "negative" image. A corresponding mold is created from the impression. This mold or a stone model created from the mold can then be scanned. A computer program is able to create a three-dimensional perspective of the relevant jaw section of the patient, including the implant and abutment. Due to the information markers on the surface of the healing abutment now present in the mold, the computer program is able to accurately analyze and produce the appropriate dimensions of the aperture in the gingiva and the orientation of the underlying hexagonal boss of the implant so that a clinician can instruct a milling machine to produce the permanent components.

In an alternative embodiment, the scanner simply takes the necessary information directly from the mouth of a patient without the need for impression material whatsoever. The information markers of the healing abutment provide the required information of the gingival aperture and the orientation of the underlying hexagonal boss on the implant. If a laser or photographic scanning system is used, the etched markers are identified just as easily as the markers that change the physical shape of the healing abutment.

This system allows the dentist to produce the permanent components more quickly because the healing abutment does not have to be removed in order to produce the permanent dental components. In other words, the second step of taking an impression with an impression coping is eliminated. The dentist also does not have to confront the difficulties of gingival closure that appear when a healing implant is removed. Finally, the patient is not forced to endure the somewhat painful procedure of healing abutment removal. With the procedure of the present invention, the removal of the healing abutment can occur during the same surgery as the installation of the permanent components.

In a further alternative embodiment, it is contemplated in accordance with the present invention that an impression coping may possess information markers as described above and replace the standard healing abutment during second stage dental restoration surgery. The impression coping and surrounding environment are scanned directly in the mouth. An impression could also be formed and a stone model produced from the impression. This stone model is scanned to create the permanent prosthesis, using one of the scanning techniques described above.

BRIEF DESCRIPTION OF THE DRAWINGS

Other objects and advantages of the invention will become apparent upon reading the following description of illustrative embodiments and upon reference to these drawings.

FIG. 1b is a longitudinal cross-sectional view of the healing abutment shown in FIG. 1a;

FIG. 2b is a longitudinal cross-sectional view of the healing abutment shown in FIG. 2a;

FIG. 3b is a longitudinal cross-sectional view of the healing abutment shown in FIG. 3a.

FIG. 4b is a longitudinal cross-sectional view of the healing abutment shown in FIG. 4a;

FIG. 5b is a longitudinal cross-sectional view of the healing abutment shown in FIG. 5a;

FIG. 6b is a longitudinal cross-sectional view of the healing abutment shown in FIG. 6a;

Figure 1B:
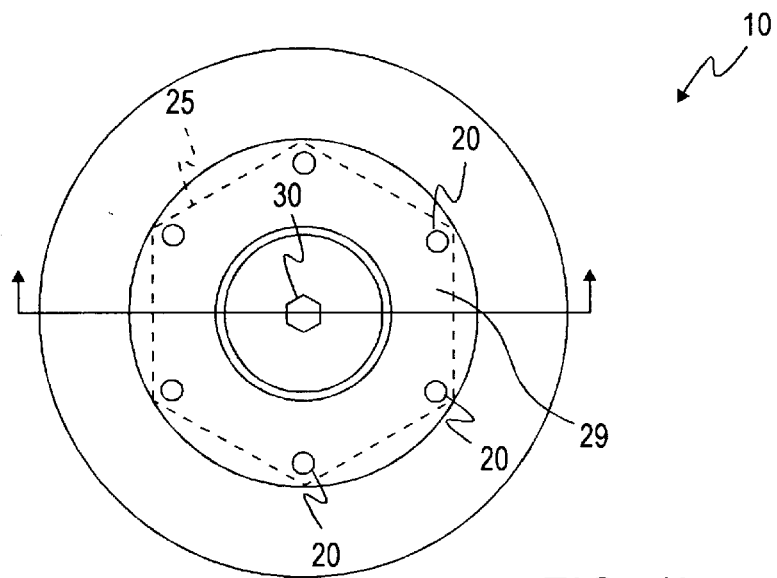

While the invention is susceptible to various modifications and alternative forms, specific embodiments thereof have been shown by way of example in the drawings and will herein be described in detail. It should be understood, however, that it is not intended to limit the invention that the particular forms disclosed, but on the contrary the invention is to cover all modifications, equivalents, and alternatives that fall within the spirit and scope of the invention as defined by the appended claims.

DESCRIPTION OF ILLUSTRATIVE EMBODIMENTS

Figure 1A:
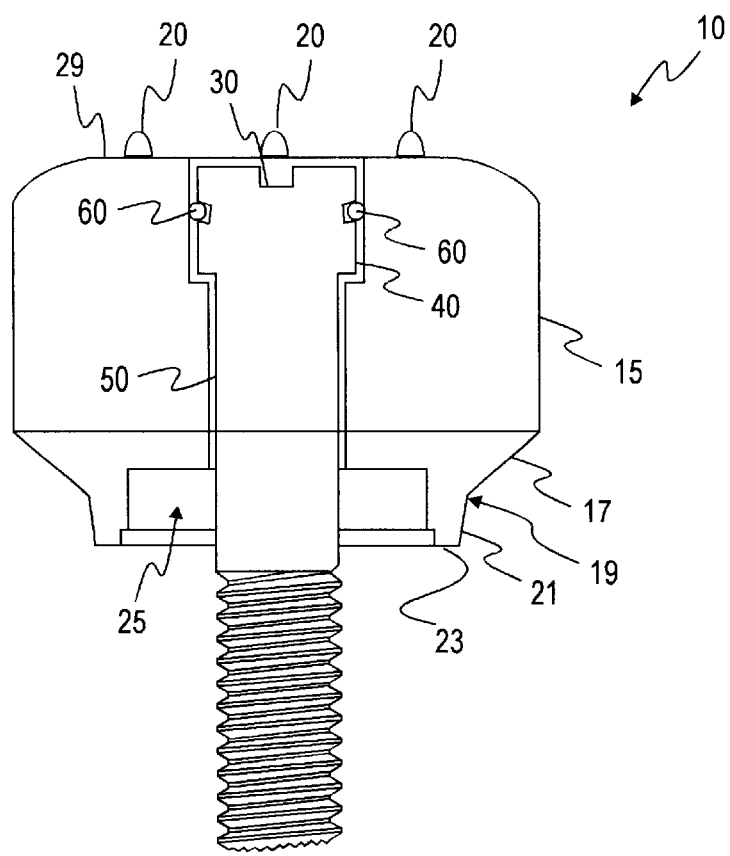
FIG. 1a is a top view of a healing abutment.

As shown in FIGS. 1a and 1b, the healing abutment 10 of one embodiment of the present invention has a main body 15 with a generally circular cross-sectional shape, a first tapered section 17, a boundary 19, a second tapered section 21, an end surface 23, a hex socket 25 and dimensions that are generally suitable for replicating the emergence profile of a natural tooth. The first tapered section 17 extends downwardly from the main body 15 of the abutment 10 having a diameter at a boundary 19 that is generally larger than the implant (not shown). The boundary 19 separates the first tapered section 17 from the second tapered section 21 that terminates in the end surface 23. The second tapered section 21 is at an angle with the central axis of the implant that is generally in the range from about 5 degrees to about 15 degrees, with 10 degrees being preferable. Alternatively, the second tapered section 21 may be omitted such that the first tapered section 17 tapers directly to the diameter of the end surface 23 of the implant. In a further embodiment, the first tapered section 17 may merge smoothly into the second tapered section 21, without the distinct boundary 19 separating the two tapered sections 17 and 21. The hexagonal orientation socket or hex 25 is for mating with a hexagonal boss on the implant. The end surface 23 has generally the same diameter as the seating surface of the implant.

FIG. 1b discloses the top view of the same healing abutment 10 shown in FIG. 1a. As shown in FIGS. 1a and 1b, the healing abutment 10 has positive information markers 20 protruding from a top surface 29 of the healing abutment 10. Each of the six positive information markers 20 is disposed such that it aligns with the six corners of the underlying hex 25. It is also contemplated in accordance with the present invention that the six information markers 20 may also correspond to the height of the healing abutment. For example, two information markers might correspond to a 2 mm tall healing abutment and four information markers might correspond to a healing abutment that is 4 mm tall. In these embodiments, the two or four information markers would still be at the corners of the underlying hex 25 so that the relative position of the hex is known.

Figure 1C:
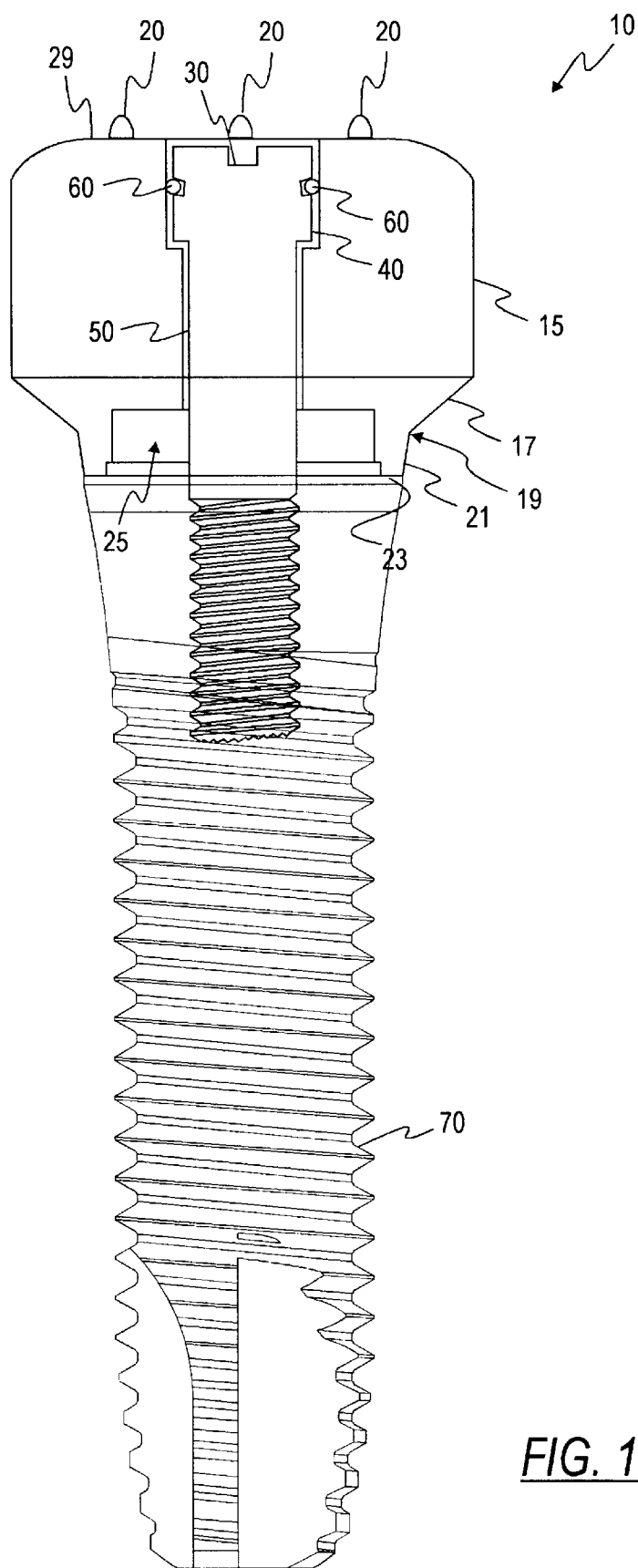
FIG. 1c is the healing abutment shown in FIG. 1b attached to an implant.

A socket 30 on the exposed surface of a head portion 40 of an attaching bolt 50 is shaped to accept a wrench (not shown) for turning the attaching bolt 50 into the threaded bore of an implant 70, as shown in FIG. 1c. It is contemplated in accordance with the present invention that each of the healing abutments described herein and shown in the figures can be secured to an implant by means of an attaching bolt, as is known in the art. An O-ring 60 carried on the head portion 40 of the attaching bolt 50 fills an annular gap left between the head and the entrance section near the outermost (widest) opening in the entrance section.

Figure 2B:
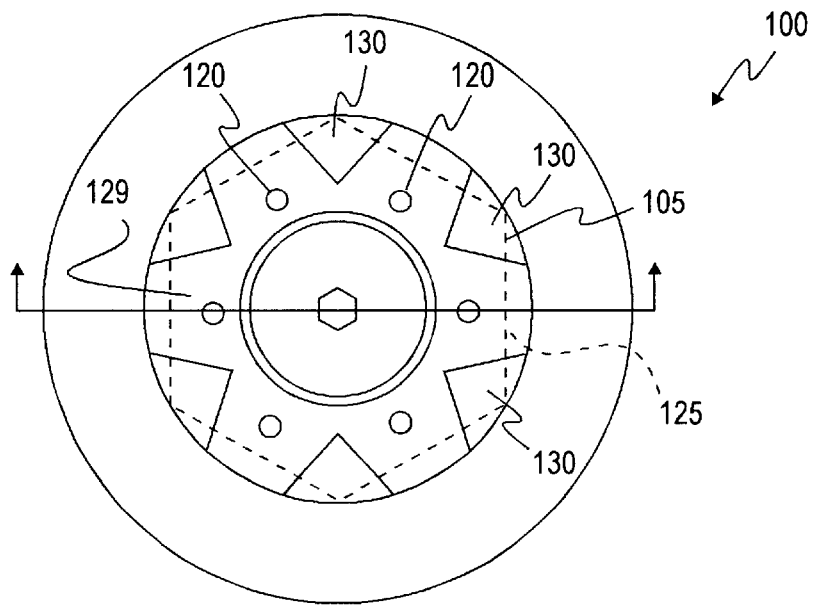
Figure 2A:
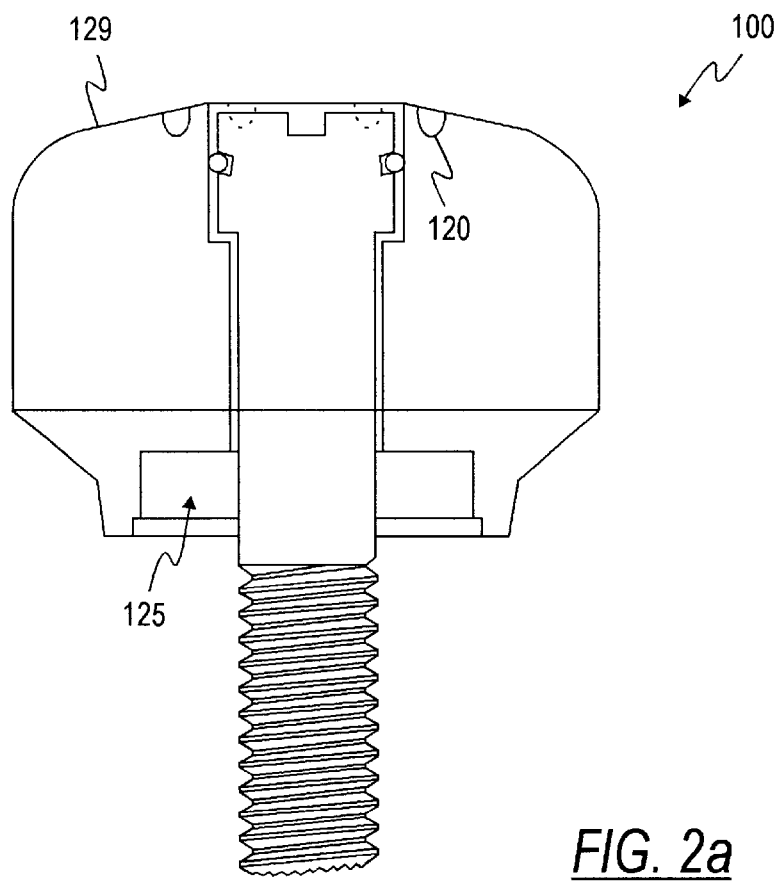
FIG. 2a is a top view of another embodiment of a healing abutment.

A healing abutment 100 of FIG. 2a comprises many of the same features as the healing abutment 10 shown in FIG. 1a. Dashed lines 125 in FIG. 2b correspond to the underlying hex 125 of the healing abutment 100 in FIG. 2a. A top surface 129 includes negative information markers (recesses) 120 that are displayed in FIG. 2a as dimples extending below the top surface 129 of the healing abutment 100. The top surface 129 of the healing abutment 100 also possesses six notches 130 that are machined into the corners. The top surface 129 is generally flat and merges into a rounded shape at the periphery of the healing abutment 100.

The notches 130 are used, for example, to determine the identification of the underlying implant hex position 125 or the height of the healing abutment or the diameter of the healing abutment. This embodiment is not limited to comprising six notches in the top surface 129 of the healing abutment 100. It is also contemplated that one embodiment of the present invention may possess four notches or even two notches for indicative purposes. Furthermore, it is contemplated that the information marker and notch approach could be combined or modified to provide information regarding the underlying implant seating surface diameter and implant hex angulation.

Figure 3B:
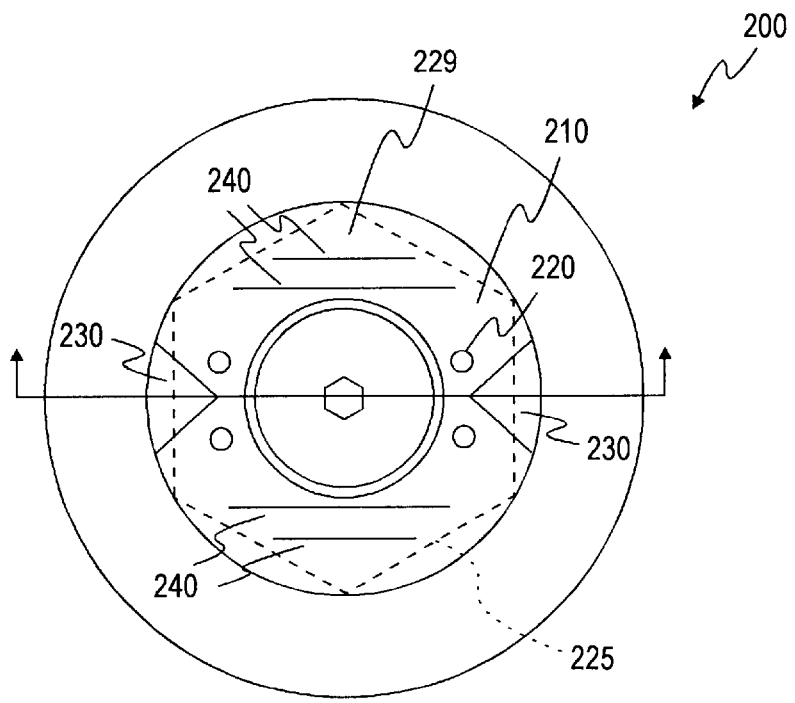
Figure 3A:
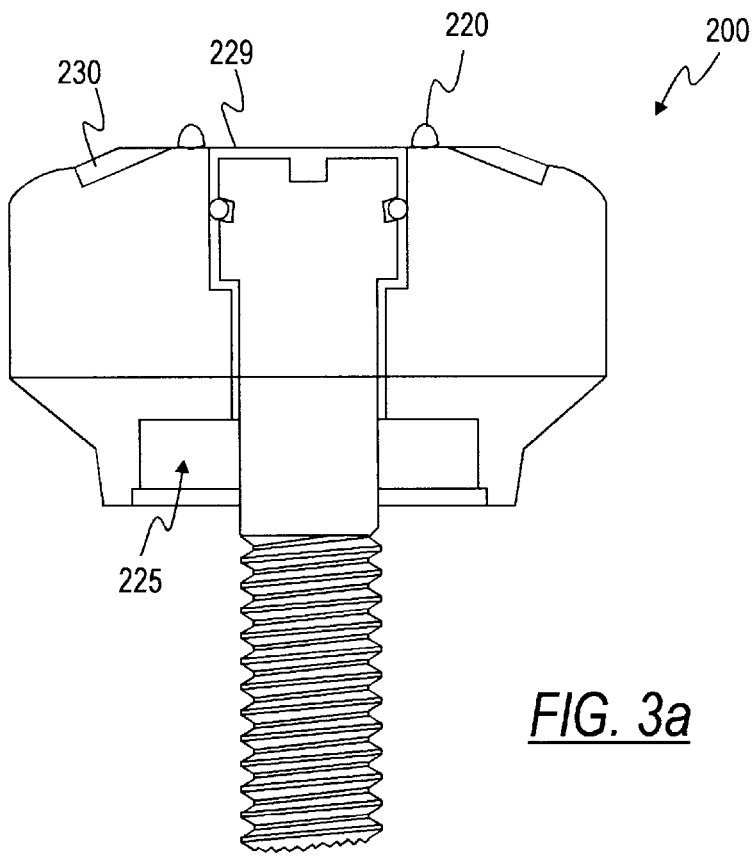
FIG. 3a is a top view of yet another embodiment of a healing abutment.

In another embodiment of the present invention, a healing abutment 200 shown in FIGS. 3a and 3b displays four positive information markers 220 shown to, for example, indicate a 4-mm tall healing abutment 200. It is contemplated that the number of information markers 220 could decrease or increase depending on the height of the healing abutment 200 or another variable that the information markers have been designated to correspond. The positive information markers 220 also define a corresponding one of the six flat surfaces of an underlying hex 225. Furthermore, dashed lines 225 in FIG. 3b correspond directly to the underlying hex 225.

Two notches 230 have also been etched or machined onto a top surface 229 of the healing abutment of FIG. 3b. These notches may indicate the diameter of the implant's seating surface. Lines 240 are scribed on the top surface 229 of the healing abutment 200. The lines 240 are used to provide positioning or other information to the dentist or laboratory. Here, the lines 240 indicate the diameter of the healing abutment (e.g., 4 mm). In summary, the number of the positive information markers 220 indicates the height of the healing abutment 200. The position of the positive information markers 220 indicates the orientation of the hex 225 that is the orientation of the hexagonal boss on the implant. The notches 230 indicate the diameter of the seating surface of the implant. The lines 240 indicate the diameter of the healing abutment 200.

Figure 4B:
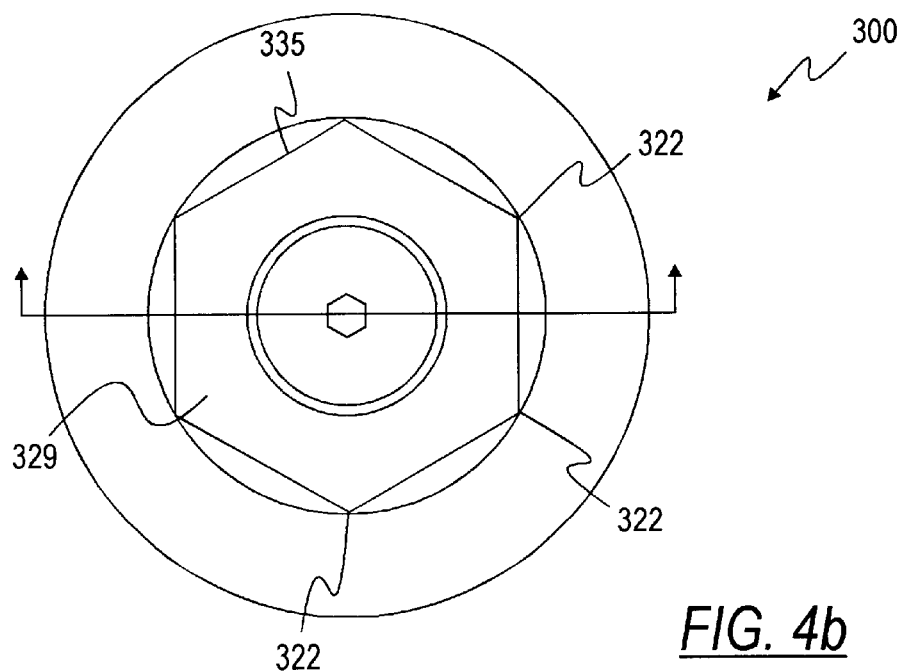
Figure 4A:
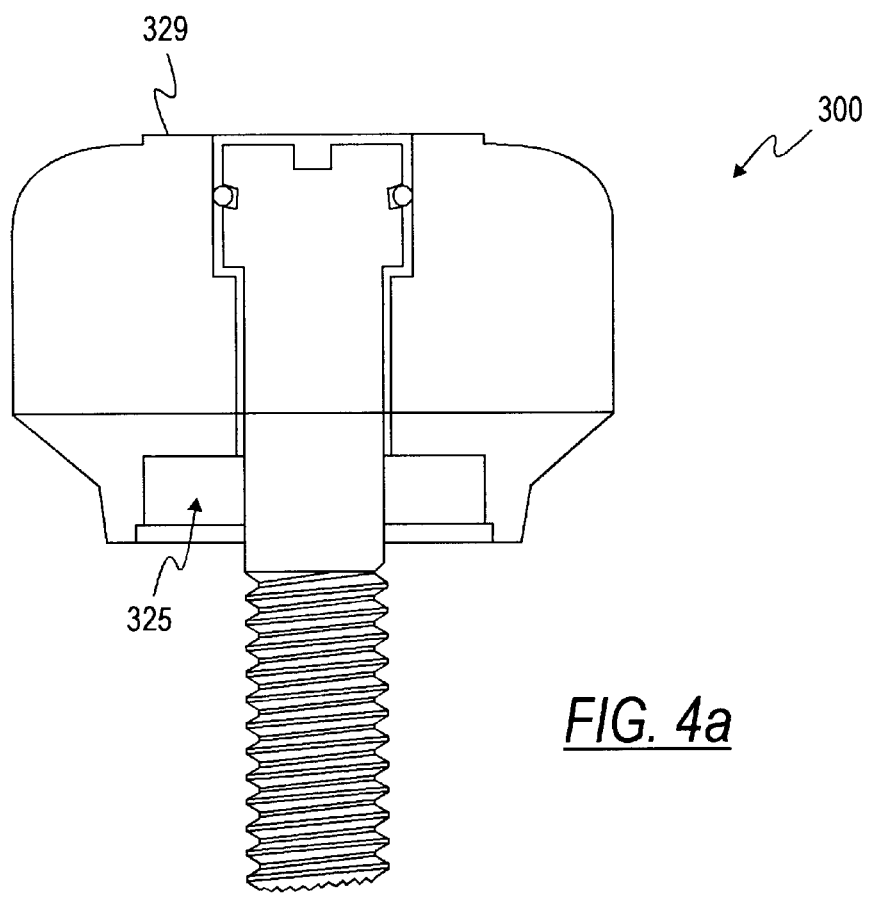
FIG. 4a is a top view of a further embodiment of the healing abutment.

In yet another embodiment of the present invention, a top surface 329 of the healing abutment 300 of FIGS. 4a and 4b comprises an etched or machined hex 335. Corners 322 of the etched hex 335 correspond directly to the position of the corners of an underlying hex 325 shown in FIG. 4a. It is contemplated in accordance with one embodiment of the present invention that further information markers may be added to the healing abutment for the dentist or laboratory to ascertain different heights or diameters.

Figure 5B:
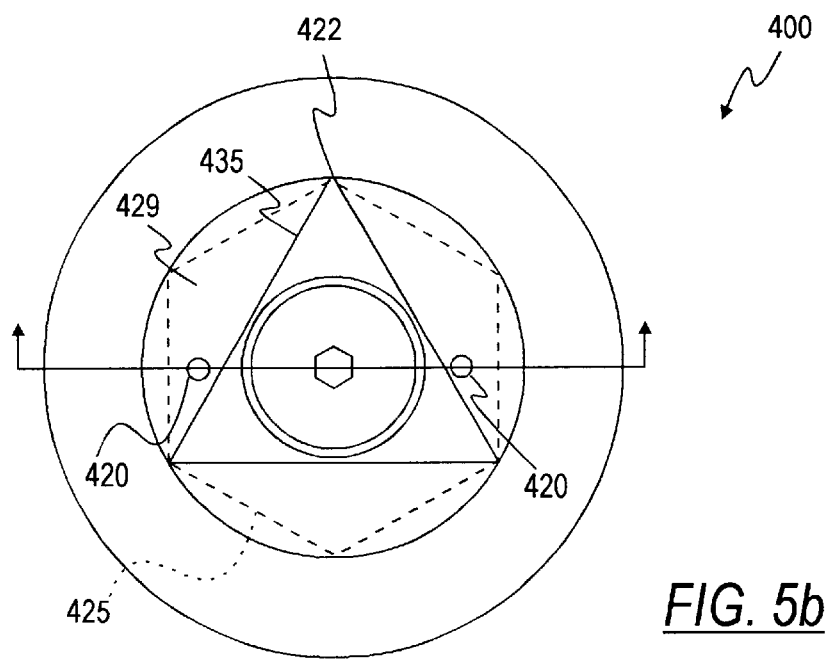
Figure 5A:
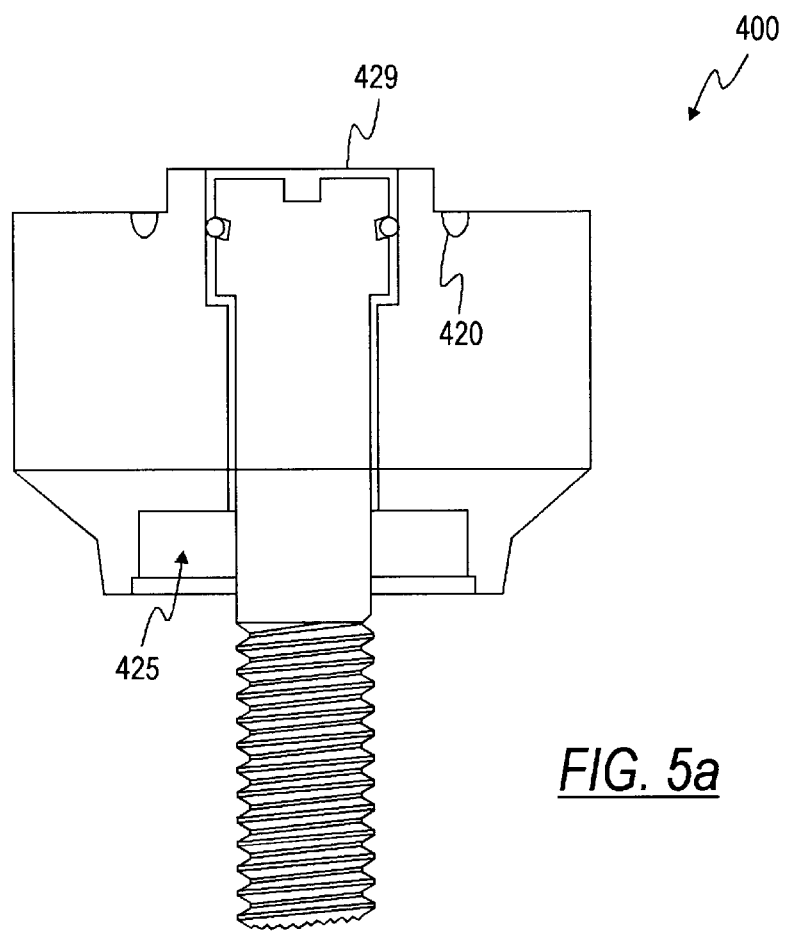
FIG. 5a is a top view of another embodiment of a healing abutment.

A top surface 429 of a healing abutment 400 shown in FIGS. 5a and 5b contains an etched or machined triangle 435. Dashed lines 425 in FIG. 5b indicate the location of an underlying hex 425. Corners 422 of the etched triangle 435 correspond to three of the six corners of the underlying hex 425. Furthermore, two negative information markers 420 are shown in FIG. 5b. As above, it is contemplated in accordance with the present invention that fewer than six information markers may exist to account for differing heights or diameters of the healing abutments.

Figure 6B:
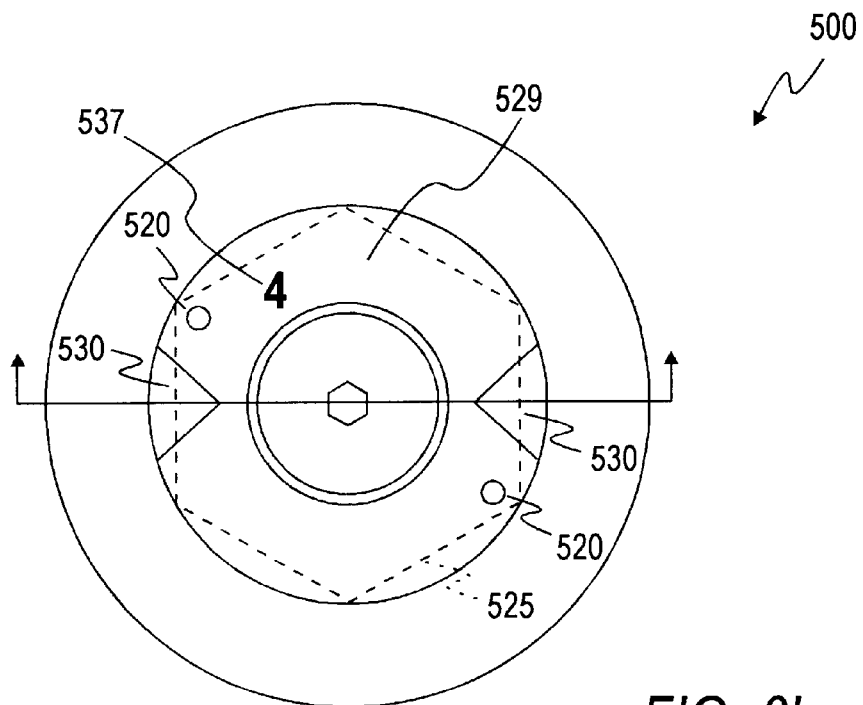
Figure 6A:
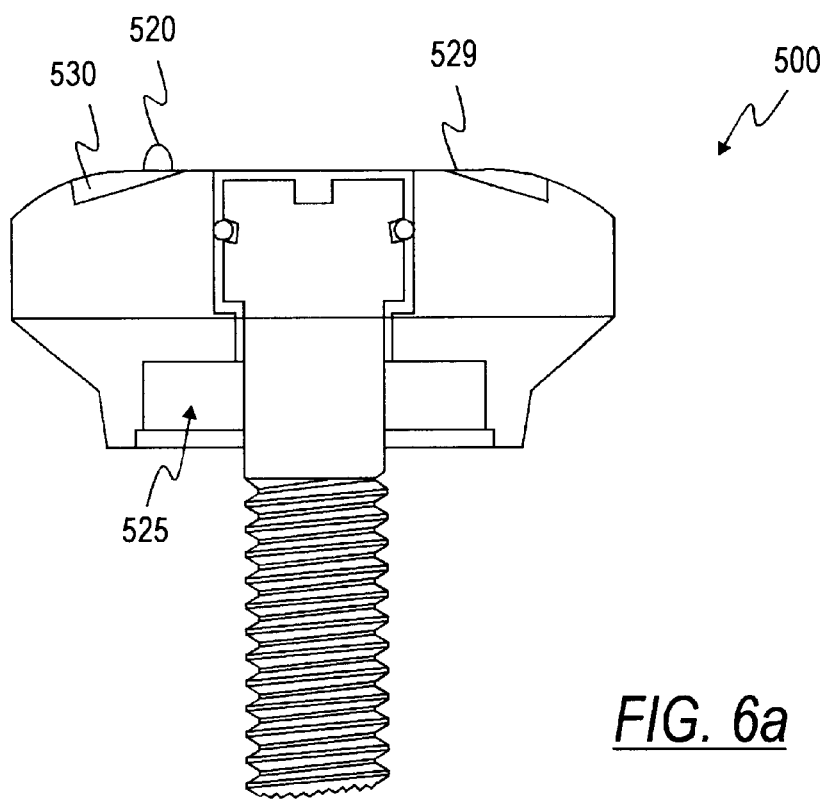
FIG. 6a is a top view of another embodiment of a healing abutment.

Another embodiment of the present invention is shown in FIGS. 6a and 6b. The healing abutment 500 displayed in FIGS. 6a and 6b is a shorter version of the healing abutment 10 shown in FIGS. 1a and 1b. Two positive information markers 520 are shown in FIG. 6b, to identify the height of the healing abutment 500. Dashed lines 525 of the healing abutment 500 correspond with the location and orientation of the underlying hex 525. Two notches 530 also are shown in a top surface 529 of this embodiment of the present invention to show the orientation of two of the underlying flats of the underlying hex 525. A numeral "4" at 537 is located on the top surface 529 of the healing abutment 500 to indicate, for example, the diameter of the healing abutment 500. As shown, the numeral "4" at 537 corresponds to a healing abutment 500 with a diameter of 4 mm. It is contemplated in accordance with the present invention that other numerals could be placed on the top surface 529 of the healing abutment 500 to indicate other healing abutment diameters. Further, it is also contemplated that the numeral could represent the height of the healing abutment or the diameter of the underlying implant.

During the second stage of the prosthetic implementation process and after a healing abutment with the information markers has been placed, an impression of the mouth is made with only the healing abutments as described herein and without the use of an impression coping. A model of the impression is poured with, for example, die stone. Since the information markers are disposed on the top and/or side of the healing abutment, the laboratory has all necessary information to define the gingival aperture, the implant size and the orientation of the underlying hex. This enables the laboratory to quickly prepare the permanent components. The system of the present invention also allows the maintenance of the soft-tissue surrounding the healing abutment where in prior systems the soft tissue would close once the healing abutment was removed. The system spares the patient from the pain of removing the healing abutment.

Figure 8:
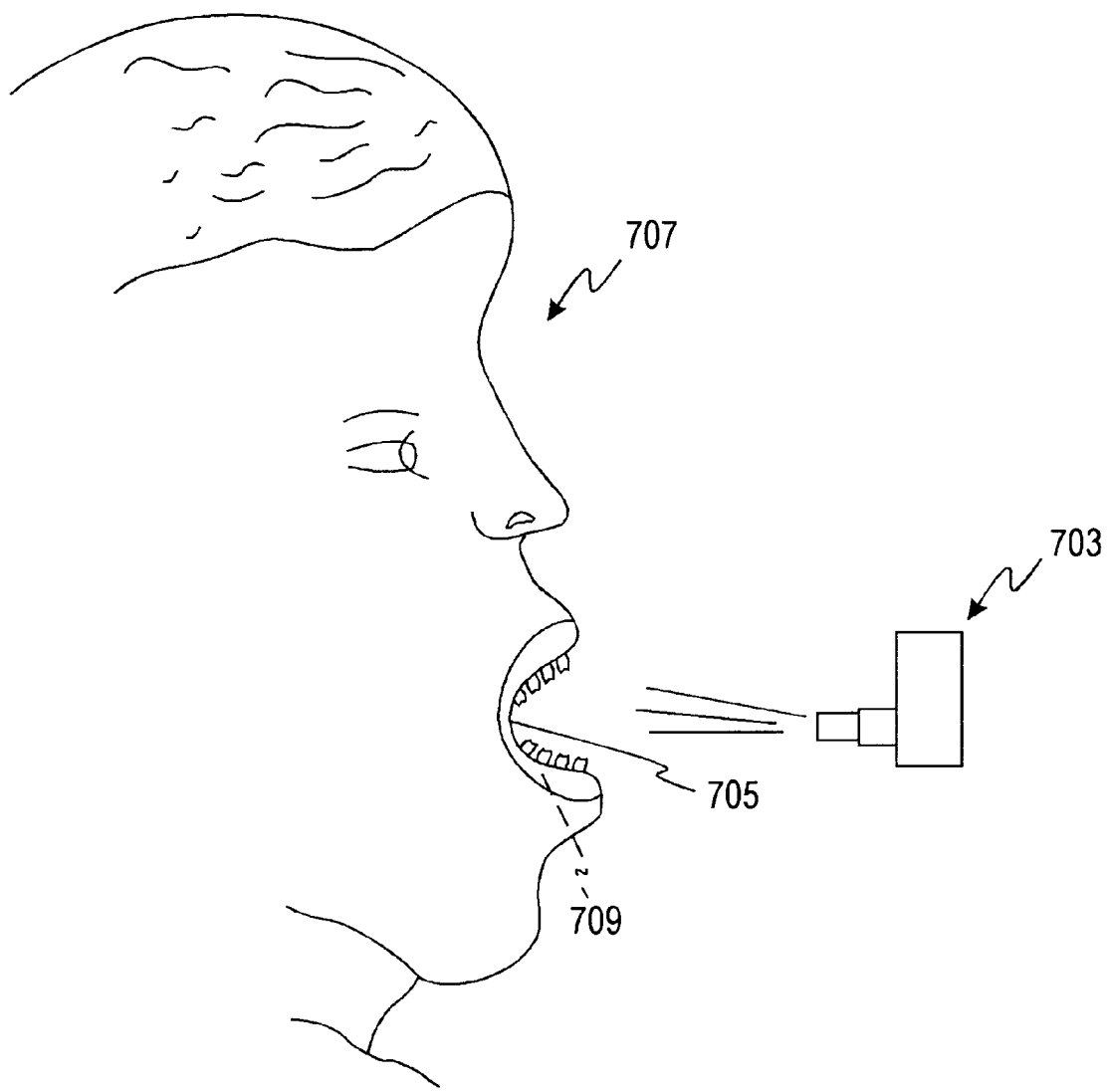
FIG. 8 is a side view of a method for stereophotographic imaging.

To create a permanent prosthesis, the dental region is scanned, as described above, from a stone model, from the impression material, or directly in the mouth using a laser scanning technique, a photographic scanning technique or a mechanical sensing technique. FIG. 8 shows stereophotographic imaging, one method used for scanning. Stereophotography with a camera 703 is performed directly on the mouth cavity 705 of the patient 707. A clinician can photograph implants and other components that have been placed into or adjacent the patient's jawbone 709.

The scanned information is then transferred into a graphical imaging program for analysis. The graphical imaging software program, due to the information markers on the surface of the healing abutment, can perform a wide variety of functions. The graphical imaging program can scan an opposing cast in order to develop an opposing occlusal scheme and relate this information back to the primary model. This feature is extremely important because many clinical patients have implants in both maxillary and mandibular locations.

The graphical imaging software program is capable of generating a three-dimensional image of the emergence profile contours used on the healing abutment. If the implant is not placed in the desired esthetic location, the software program relocates the position of the restoration emergence through the soft tissue. The graphical imaging software program is also able to accurately relate the gingival margin for all mold, model, implant and abutment dimensions. The software creates a transparent tooth outline for superimposition within the edentulous site. The occlusal outline of the "ghost" tooth should, if possible, be accurate and based on the scanned opposing occlusal dimensions. It is contemplated in accordance with the present invention that an occlusal outline is created by scanning a wax-up in order to maintain a proper plane of occlusion and healing abutment height.

The software program subtracts a given dimension from the mesial, distal, buccal, lingual, and occlusal areas of the superimposed tooth dimension. This allows for an even reduction of the healing abutment during fabrication to allow for proper thickness of the overlying materials (e.g., gold, porcelain, targis, etc.). The graphical imaging software program also incorporates angulation measurements into the custom abutment and subsequently calculates the dimensions of the prosthesis that are checked and modified, if necessary, by a laboratory technician. Each of the features is analyzed and determined from the different information markers that exist on the healing abutments of the present invention.

The final dimensional information determined by the graphical imaging computer program is transferred from the computer to a milling machine (e.g., a 5-axis milling machine) to fabricate the custom abutment. It is contemplated in accordance with the present invention that the custom abutment can be fashioned from gold or titanium or other similar metals or composites. A custom milled coping can then be fabricated. It is contemplated in accordance with the present invention that the custom milled coping can be formed from titanium, plastic, gold, ceramic, or other similar metals and composites.

Figure 7:
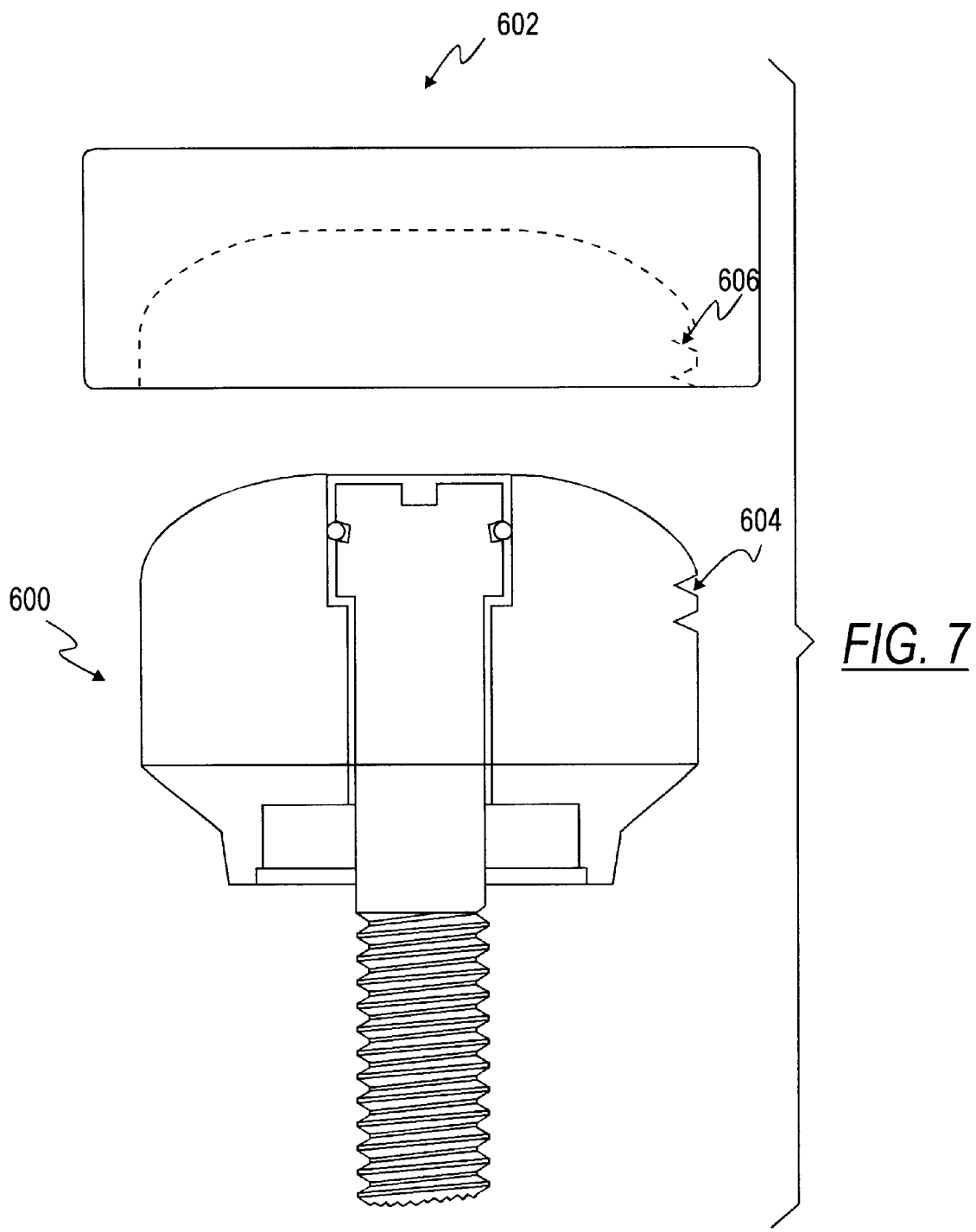
FIG. 7 is an exploded view of another embodiment of the present application.

FIG. 7 shows the exploded view of another embodiment of the present invention. A cap 602 is placed on a healing abutment 600 and later removed during the process of taking the impression of the healing implant and surrounding features of the patient's mouth. It is contemplated in accordance with the present invention that the cap 602 could be formed from plastic or metal or a composite material. As shown in FIG. 7, notches 604 are formed in the side(s) of the healing abutment 600. These notches correspond to notches 606 that have been preformed in the cap 602. When the cap 602 is placed onto the healing abutment 600, the cap only fits snugly and properly if the number of notches 606 in the cap 602 corresponds exactly to the number of notches 604 in the side wall(s) of the healing abutment. It is contemplated in accordance with the present invention that there could be many less or more notches than is depicted in FIG. 7. These notches correspond to information parameters such as healing abutment height, healing abutment and/or implant diameter and other parameters as listed above.

Specifically, after the healing abutment has been secured to the implant, the cap 602 is securely placed over the top of the healing abutment 600. The impression material is then placed over the top of the cap 602. The impression is then either scanned in the patient's mouth or the impression material (with the cap 602) is then scanned and the process continues as described above.

While the present invention has been described with references to one or more particular embodiments, those skilled in the art will recognize that many changes may be made thereto without departing from the spirit and scope of the present invention. Each of these embodiments and obvious variations thereof is contemplated as falling within the spirit and scope of the present invention, which is set forth in the following claims.

What is claimed is:

1. A method of developing a prosthetic tooth, said method comprising: installing a dental implant into a jawbone;
   attaching a gingival healing element to said dental implant, said healing element having a top surface, a side surface for engaging gingiva, and at least two information markers on said top surface that allow identification of at least two characteristics of said gingival healing element;
   determining said at least two characteristics of said gingival healing element to gather information for manufacturing said prosthetic tooth, and
   developing said prosthetic tooth based on said at least two characteristics.

2. The method of claim 1, wherein said markers are one of a group consisting of positive information markers, negative information markers, polygonal markers, numerical markers, line markers, machined or etched markers, and barcode markers.

3. The method of claim 2, wherein said barcode markers are precoded with multiple pieces of information of said healing element.

4. The method of claim 3, wherein a barcode reader interprets said information markers contained within said precoded information.

5. The method of claim 1, wherein said information markers include raised pimples.

6. The method of claim 1, wherein said information markers include recessed dimples.

7. The method of claim 1, wherein said information markers include polygonal markers.

8. The method of claim 7, wherein said polygonal markers are in the shape of a triangle, a pentagon, a hexagon, or a quadrilateral.

9. The method of claim 1, wherein said characteristics include one or more of the height of said healing element, the diameter of said healing element, the size of said implant, and/or the orientation of a hexagonal boss of said implant.

10. The method of claim 1, wherein said determining includes scanning said markers and interpreting said markers for creation of said prosthetic tooth.

11. The method of claim 10, wherein said scanning step is accomplished with a photographic imaging scanner.

12. The method of claim 10, wherein said scanning step is accomplished with a laser imaging scanner.

13. The method of claim 10, wherein said scanning step is accomplished with a mechanical sensing scanner.

14. The method of claim 1, wherein said determining includes taking an impression of a region of a mouth where said gingival healing element is located.

15. The method of claim 14, wherein said determining further includes scanning a stone model of said region formed from said impression.

16. A method of taking an impression and scanning an image to form a prosthetic tooth of a region in a mouth being located adjacent to an implant installed into a jawbone having overlying gingiva, said implant having an apical end installed into said jawbone and a gingival end near an interface of said gingiva and said jawbone with a hexagonal boss thereon, said method comprising the steps of:

exposing said gingival end of said implant through said gingiva;

attaching a gingival forming component to said gingival end of said implant;

allowing said gingiva to heal around said gingival forming component, without adding an additional component to said gingival forming component, taking an impression of said region; and scanning information from the impression into an information-receiving device.

17. The method of claim 16, wherein said impression taking step is performed with impression material, said impression material engaging said gingival forming component.

18. The method of claim 17, wherein said impression taking step is performed by scanning said impression material after being removed from said region.

19. The method of claim 17, wherein said impression taking step is performed by scanning a stone model of said region formed from said impression material.

20. The method of claim 16, wherein said scanning step is performed by a photographic imaging scanner.

21. The method of claim 16, wherein said scanning step is performed by a laser imaging scanner.

22. The method of claim 16, wherein said scanning step is performed by a mechanical sensing scanner.

23. A healing element for attachment to a dental implant, said healing element comprising:
(1) a top surface;
(2) a side surface for engaging gingiva;
(3) a first type of marking indicative of a first characteristic of said healing element, said first type of marking includes a surface protruding outwardly from said top surface; and
(4) a second type of marking indicative of a second characteristic of said healing element, said second type of marking being different from said first type of marking.

24. A healing element for attachment to a dental implant, said healing element comprising:
(1) a top surface;
(2) a side surface for engaging gingiva;
(3) a first type of marking indicative of a first characteristic of said healing element, said first characteristic is an orientation of a polygonal socket within said healing element, said polygonal socket is a hexagonal socket and said first type of marking includes at least two features on said top surface, each of said at least two features being located, relative to a central axis of said healing element, at the same circumferential position as one of the six corners of said hexagonal socket; and
(4) a second type of marking indicative of a second characteristic of said healing element, said second type of marking being different from said first type of marking.

25. The healing element of claim 24, wherein said first type of marking includes four features on said top surface, each of said four features being located, relative to a central axis of said healing element, at the same circumferential position as one of the six corners of said hexagonal socket.

26. The healing element of claim 25, wherein said first type of marking includes six features on said top surface, each of said six features being located, relative to a central axis of said healing element, at the same circumferential position as a corresponding one of the six corners of said hexagonal socket.

27. A healing element for attachment to a dental implant, said healing element comprising:
(1) a top surface;
(2) a side surface for engaging gingiva;
(3) a first type of marking indicative of a first characteristic of said healing element, said first characteristic is an orientation of a polygonal socket within said healing element, said first type of marking includes at least two features on said top surface located at positions which indicate locations of the corners of said polygonal socket; and
(4) a second type of marking indicative of a second characteristic of said healing element, said second type of marking being different from said first type of marking.

28. A method of developing a prosthetic tooth, said method comprising attaching a healing element to a dental implant, said healing element comprising a singular type of marking indicative of first and second characteristics of said healing element;

determining said first and second characteristics of said healing element to gather information for manufacturing said prosthetic tooth; and developing said prosthetic tooth based on said first and second characteristics.

29. The method of claim 28, wherein said first characteristic is an orientation of a polygonal socket within said healing element and said second characteristic is a height of said healing element.

30. The method of claim 28, wherein said first characteristic is a diameter of said healing element and said second characteristic is an orientation of a polygonal socket within said healing element.

31. A method of developing a prosthetic tooth, comprising:

installing a dental implant into a jawbone having overlying gingiva;

installing a gingival healing abutment on said implant so as to extend through said gingiva, said gingival healing abutment having first and second markings indicative of first and second characteristics of said gingival healing abutment;

allowing said gingiva to heal around said gingival healing abutment; and scanning a region of a mouth where said gingival healing abutment is located to obtain said first and second markings which are indicative of said first and second characteristics.

32. A method of developing a prosthetic tooth, comprising:

installing a dental implant into a jawbone having overlying gingiva;

installing a gingival healing abutment on said implant so as to extend through said gingiva, said gingival healing abutment having a first type of marking indicative of an orientation of a polygonal feature of said gingival healing abutment; and without adding an additional component to said gingival healing abutment, taking an impression of a region of a mouth where said gingival healing abutment is located.

33. The method of claim 32 wherein said first type of marking indicates a height of said gingival healing abutment.

34. The method of claim 32, further including the step of scanning said impression.

35. The method of claim 34, wherein said scanning step is performed by a photographic imaging scanner.

36. The method of claim 34, wherein said scanning step is performed by a laser imaging scanner.

37. The method of claim 34, wherein said scanning step is performed by a mechanical sensing scanner.

38. The method of claim 34, wherein said scanning step is performed by scanning a stone model of said region formed from said impression.

39. A set of dental healing elements, each of said healing elements having unique physical characteristics and at least two information markers on a surface of each of said healing elements, each of said information markers providing information regarding said unique physical characteristics of each of said healing elements, said unique physical characteristics of each of said healing elements being identifiable through said information markers.

40. The set of claim 39, wherein said unique characteristics include a height of said healing element.

41. The set of claim 39, wherein said unique characteristics include a diameter of a seating surface of said healing element.

42. The set of claim 39, wherein said information markers are selected from positive information markers, negative information markers, polygonal markers, numerical markers, line markers, machined or etched markers, and barcode markers.

* * * * *